(12) United States Patent
Hamada

(10) Patent No.: US 7,393,951 B2
(45) Date of Patent: Jul. 1, 2008

(54) ANTISENSE OLIGONUCLEOTIDE HAVING ANTICANCEROUS ACTIVITY

(75) Inventor: Katsutomo Hamada, Hiroshima (JP)

(73) Assignee: Good Will Okinawa Co., Ltd., Naha-shi (JP)

( * ) Notice: Subject to any disclaimer, the term of this patent is extended or adjusted under 35 U.S.C. 154(b) by 239 days.

(21) Appl. No.: 10/558,265

(22) PCT Filed: Oct. 27, 2004

(86) PCT No.: PCT/JP2004/015932

§ 371 (c)(1),
(2), (4) Date: Nov. 21, 2005

(87) PCT Pub. No.: WO2005/071082

PCT Pub. Date: Aug. 4, 2005

(65) Prior Publication Data

US 2007/0129318 A1    Jun. 7, 2007

(30) Foreign Application Priority Data

Jan. 22, 2004  (JP) .............................. 2004-014883

(51) Int. Cl.
C07H 21/04    (2006.01)
(52) U.S. Cl. .................................. 536/24.5
(58) Field of Classification Search ............... None
See application file for complete search history.

(56) References Cited

U.S. PATENT DOCUMENTS 5,827,705 A * 10/1998 Dean ........................ 435/458
5,985,558 A * 11/1999 Dean et al. ...................... 435/6
6,130,207 A * 10/2000 Dean et al. ...................... 514/44
6,566,514 B1 * 5/2003 Wright et al. ............... 536/24.5
2003/0232443 A1   12/2003 Bennett et al.

FOREIGN PATENT DOCUMENTS

WO    WO-94/08003 A1    4/1994
WO    WO-02/44332 A2    6/2002

OTHER PUBLICATIONS

Hamada et al., J. Biol. Chem., 1999, vol. 274, No. 22, pp. 15786-15796.
Ullu, E et al., Nature, 1984, vol. 312, No. 5990, pp. 171-172.
Liu L et al., J. Biol. Chem., 2003, vol. 278, No. 20, pp. 18271-18280.
Hamada et al., *Mollecular and Cellular Biology*, vol. 9, No. 10, Oct. 1989, pp. 4345-4356.
Hamada, *Molecular Carcinogenesis*, 20:175-188 (1997).

* cited by examiner

*Primary Examiner*—Richard Schnizer
(74) *Attorney, Agent, or Firm*—Birch, Stewart, Kolasch & Birch, LLP

(57) ABSTRACT

An antisense oligonucleotide having anti-carcinogenicity, for example, an inhibitory action on growth of cancer cells and a therapeutic or prophylactic action on cancer and the like, as well as an inhibitor of cancer cell growth and a therapeutic or prophylactic agent for cancer, which comprise the antisense oligonucleotide are provided.

An antisense oligonucleotide to a nucleotide sequence of positions 47 to 51 of 7SL RNA of the signal recognition particle (SRP), an inhibitor of cancer cell growth comprising the antisense oligonucleotide, and a therapeutic or prophylactic agent for cancer comprising the antisense oligonucleotide.

5 Claims, 5 Drawing Sheets

SEQUENCE LISTING

```
<160> NUMBER OF SEQ ID NOS: 9

<210> SEQ ID NO 1
<211> LENGTH: 5
<212> TYPE: DNA
<213> ORGANISM: Artificial Sequence
<220> FEATURE:
<223> OTHER INFORMATION: Antisense oligonucleotide corresponding to
      nucleotides 47-51 of 7SL RNA

<400> SEQUENCE: 1 cctca                                                                       5

<210> SEQ ID NO 2
<211> LENGTH: 29
<212> TYPE: RNA
<213> ORGANISM: Homo sapiens

<400> SEQUENCE: 2
gauuuccgug gagaggaaca acucugagu                                            29

<210> SEQ ID NO 3
<211> LENGTH: 9
<212> TYPE: RNA
<213> ORGANISM: Artificial Sequence
<220> FEATURE:
<223> OTHER INFORMATION: A partial nucleotide sequence of Transforming
      RNA

<400> SEQUENCE: 3 ggagaggaa                                                                   9

<210> SEQ ID NO 4
<211> LENGTH: 9
<212> TYPE: DNA
<213> ORGANISM: Artificial Sequence
<220> FEATURE:
<223> OTHER INFORMATION: Oligodeoxynucleotide corresponding to the
      partial nucleotide sequence of Transforming RNA

<400> SEQUENCE: 4 ggagaggaa                                                                   9
```

```
<210> SEQ ID NO 5
<211> LENGTH: 4
<212> TYPE: DNA
<213> ORGANISM: Artificial Sequence
<220> FEATURE:
<223> OTHER INFORMATION: A partial nucleotide sequence of
      oligodeoxynucleotide

<400> SEQUENCE: 5 ggag                                                                    4

<210> SEQ ID NO 6
<211> LENGTH: 9
<212> TYPE: DNA
<213> ORGANISM: Artificial Sequence
<220> FEATURE:
<223> OTHER INFORMATION: Antisense oligodeoxynucleotide corresponding to
      the nucleotide sequence of oligodeoxynucleotide

<400> SEQUENCE: 6 ttcctctcc                                                               9

<210> SEQ ID NO 7
<211> LENGTH: 4
<212> TYPE: DNA
<213> ORGANISM: Artificial Sequence
<220> FEATURE:
<223> OTHER INFORMATION: A partial nucleotide sequence of antisense
      oligodeoxynucleotide

<400> SEQUENCE: 7 cctc                                                                    4

<210> SEQ ID NO 8
<211> LENGTH: 4
<212> TYPE: RNA
<213> ORGANISM: Rabbit

<400> SEQUENCE: 8 gagg                                                                    4

<210> SEQ ID NO 9
<211> LENGTH: 299
<212> TYPE: RNA
<213> ORGANISM: Homo sapiens

<400> SEQUENCE: 9
gccgggcgcg guggcgcgug ccuguagucc cagcuacucg ggaggcugag gcuggaggau        60
cgcuugagcu caggaguucu gggcugcagu gcgcuaugcc gaucgggugu ccgcacuaag      120
uucggcauca auaugguguc cucccgggag cgggggacca ccagguugcc uaaggagggg      180
ugaaccggcc caggucggaa acggagcagg ucaaaacucc cgucugauc aguaguggga       240 ucgcgccugu gaauagccac ugcacuccag ccugggcaac auagcgagac cccgucucu       299
```

ANTISENSE OLIGONUCLEOTIDE HAVING ANTICANCEROUS ACTIVITY

TECHNICAL FIELD

The present invention relates to an antisense oligonucleotide having anti-carcinogenicity, for example, an inhibitory action on growth of cancer cells and a therapeutic or prophylactic action on cancer and the like, as well as an inhibitor of cancer cell growth and a therapeutic or prophylactic agent for cancer, which comprise the antisense oligonucleotide.

BACKGROUND ART

Signal recognition particles (SRPs) are involved in synthesis of secretory protein in animal cells. SRP has a sedimentation coefficient of 11S as a whole and consists of 7SL RNA and 6 kinds of proteins.

Synthesis of secretory protein is initiated by binding of its mRNA to a free ribosome. The ribosome is a place for protein synthesis and consists of a rRNA and a large number of ribosomal proteins. In the case of eucaryotes, the ribosome has a sedimentation coefficient of 80S as a whole, and is further divided into 2 particles having sedimentation coefficients of 60S and 40S respectively, and the former has one molecule each of 5S, 5.8S and 28S rRNAs and the latter has one molecule of 18S rRNA.

SRP recognizes a signal peptide consisting of a hydrophobic amino acid sequence present in the N-terminal or in the vicinity of the N-terminal of a secretory protein precursor extended from the ribosome, and binds to a protein/ribosome complex. Succeeding translation of the protein is thereby terminated. SRP transports the complex to a membrane of an endoplasmic reticulum and binds to an SRP receptor protein present in the cytosol side of the endoplasmic reticulum. When the SRP-bound complex binds to the membrane, inhibition of the translation is canceled, thereby dissociating SRP to fix the ribosome to the membrane. Then, the translation is continued to allow a polypeptide chain to pass through the membrane to produce a mature secretory protein.

On the other hand, in the nucleus of the eucaryotic cell, not only mRNA and the like involved in translation of a protein as described above but also a group of RNAs called small nuclear RNAs of about 100 to 300 bases in length are synthesized. Usually, these bind to proteins and occur as ribonucleic proteins. For example, RNAs called U1, U2, U3, U4, U5 or U6 are known as the small nuclear RNAs. With respect to functions of the small nuclear RNAs, it has been revealed that U1, U2, U4, U5 and U6 participate in splicing of mRNA precursors, but other functions have not been well known yet.

Although there are thus many unrevealed features with respect to the functions of the small nuclear RNAs, it has been reported that U5 RNA cancerates cultured cells by transfection (see Non-Patent Publication 1). It has also been revealed that a transcript (transforming RNA) having poly(A) added to a nucleotide sequence (SEQ ID NO: 2) at the 3'-terminal side of a first stem in a secondary structure of U5 RNA, which was transcribed in a way dependent on RNA polymerase II, also similarly has a canceration ability (see Non-Patent Publication 2). This canceration ability was dependent on a specific nucleotide sequence (SEQ ID NO: 3) in the transforming RNA.

In a protein synthesis experiment using a rabbit reticulocyte extract, the transforming RNA suppressed synthesis of a secretory protein (see Non-Patent Publication 3). An oligodeoxynucleotide (ODN) having a nucleotide sequence set forth in SEQ ID NO: 4 also suppressed synthesis of a secretory protein in the rabbit reticulocyte extract. Furthermore, it was revealed that a specific part of nucleotide sequence (SEQ ID NO: 5) in the ODN binds to ribosomal 28S RNA. On the other hand, it was reported that an antisense oligodeoxynucleotide (antisense ODN; SEQ ID NO: 6) of the ODN binds to 7SL RNA in SRP and works for lowering suppression of secretory protein synthesis (resulting in enhancement of secretory protein synthesis), and also that a specific part of nucleotide sequence (SEQ ID NO: 7) in the antisense ODN binds to a nucleotide sequence (SEQ ID NO: 8) of positions 48 to 51 of 7SL RNA (see FIG. 1).

These reports suggest that the nucleotide sequence present in U5 RNA exhibits a canceration ability and an ability to suppress synthesis of a secretory protein as new functions, and simultaneously the antisense ODN to the part of nucleotide sequence presumed to participate in exhibition of the canceration ability and the like of U5 RNA has an action of suppressing the canceration ability and the like of U5 RNA, but which element is necessary and sufficient for suppression of the canceration ability and the like of U5 RNA is still unrevealed.

Non-Patent Publication 1: *Mol. Cell. Biol.,* 9, 4345-4356 (1989)

Non-Patent Publication 2: *Mol. Carcinog.* 20, 175-188 (1997)

Non-Patent Publication 3: *J. Biol. Chem.* 274(22), 15786-15796 (1999)

DISCLOSURE OF INVENTION

Problems to be Solved by the Invention

The object of the present invention is to provide an antisense oligonucleotide having anti-carcinogenicity, for example, an inhibitory action on growth of cancer cells and a therapeutic or prophylactic action on cancer and the like, as well as an inhibitor of cancer cell growth and a therapeutic or prophylactic agent for cancer, which comprise the antisense oligonucleotide.

Means to Solve the Problems

As described above, it was suggested that the antisense ODN to the part of nucleotide sequence presumed to participate in exhibition of the canceration ability and the like of U5 RNA has an action of suppressing the canceration ability and the like of U5 RNA, but which element is necessary and sufficient for suppression of the canceration ability and the like of U5 RNA is still unrevealed.

Accordingly, the present inventor made extensive study, and revealed for the first time that an antisense oligonucleotide to a nucleotide sequence of positions 47 to 51 of 7SL RNA of the signal recognition particle (SRP) can unexpectedly exhibit a significant effect on suppression of the canceration ability and the like of U5 RNA, thus arriving at completion of the present invention.

Specifically, on the basis of elucidation of initial functions related to the canceration ability of U5 RNA and the transforming RNA derived from U5 RNA, the present invention was made by searching for and revealing a substance acting antagonistically, thus exhibiting a lethal action, an action of suppressing growth and the like of human cancer cells.

The present invention provides:

[1] an antisense oligonucleotide to a nucleotide sequence of positions 47 to 51 of 7SL RNA of a signal recognition particle (SRP),

[2] the antisense oligonucleotide according to the item [1] mentioned above, comprising the nucleotide sequence shown in SEQ ID NO: 1,

[3] an inhibitor of cancer cell growth comprising the antisense oligonucleotide as defined in the item [1] or [2] mentioned above,

[4] a therapeutic or prophylactic agent for cancer comprising the antisense oligonucleotide as defined in the item [1] or [2] mentioned above,

[5] the therapeutic or prophylactic agent according to the item [4] mentioned above, wherein the antisense oligonucleotide is present in a liposome,

[6] the therapeutic or prophylactic agent according to the item [4] or [5] mentioned above, wherein the antisense oligonucleotide is ligated to a vector, and

[7] a method for using the antisense oligonucleotide according to the item [1] or [2] mentioned above for production of the inhibitor of cancer cell growth as defined in the item [3] mentioned above or the therapeutic or prophylactic agent as defined in any of the items [4] to [6] mentioned above.

EFFECTS OF THE INVENTION

The antisense oligonucleotide of the present invention can be used for suppressing growth of cancer cells or killing cancer cells, relieving or ameliorating the symptom of a cancer, treating or preventing a cancer, and the like.

BEST MODE FOR CARRYING OUT THE INVENTION

In this specification, the "nucleotide" is used in meaning to encompass DNA and RNA. The "antisense oligonucleotide" refers to an oligonucleotide having a nucleotide sequence complementary to a specific nucleotide sequence (hereinafter referred to as a sense sequence) and capable of hybridizing with the sense sequence.

Figure 1:
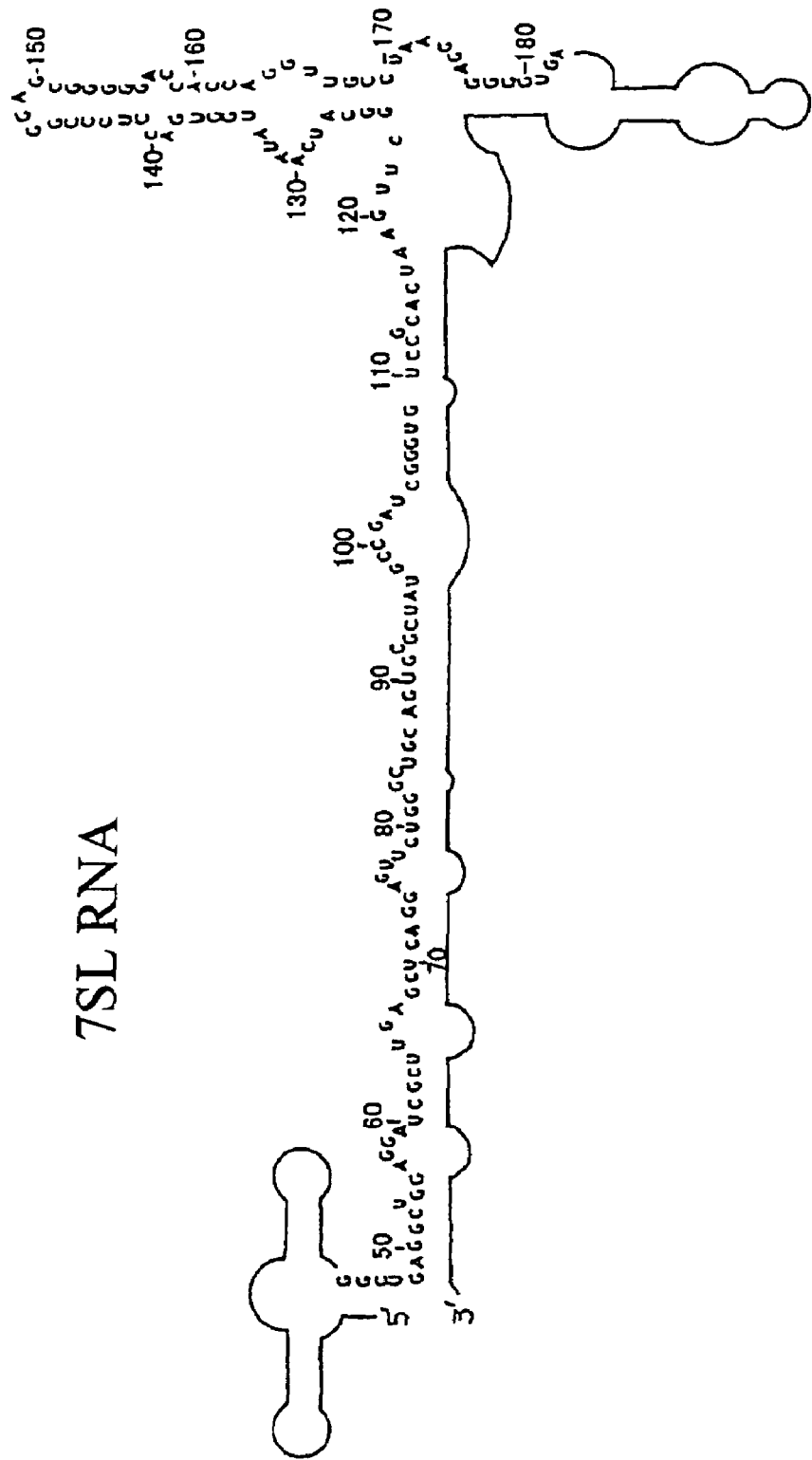
FIG. 1 (SEQ ID NO: 9) is a schematic view showing a structure of 7SL RNA of SRP derived from rabbit cells. Numbers in the figure indicate positions of bases (excluding 3' and 5').

The sense sequence corresponding to the antisense oligonucleotide of the present invention is a nucleotide sequence of positions 47 to 51 of 7SL RNA of SRP. FIG. 1 shows a schematic structure of 7SL RNA of SRP derived from rabbit cells. As the nucleotide sequence of 7SL RNA, nucleotide sequences derived from various animal cells are known. For example, the above-mentioned nucleotide sequence derived from rabbit cells is described in *J. Biol. Chem.* 274(22), 15786-15796 (1999), and a nucleotide sequence of 7SL RNA of SRP derived from human cells is described in Ullu, E., and Wiener, A. M., *EMBO J.,* 3, 3303-3310 (1984). Nucleotide sequences of 7SL RNA derived from other animals are described for example in Larzen, N., and Zwieb, C., *Nucleic Acids Res.,* 19, 209-215 (1991). The nucleotide sequences derived from at least mammalian cells have the same nucleotide sequence of positions 47 to 51 of the 7SL RNA.

The antisense oligonucleotide of the present invention has anti-carcinogenicity, for example an inhibitory action on growth of cancer cells, a therapeutic or prophylactic action on cancer and the like. Particularly, an antisense oligonucleotide comprising the nucleotide sequence shown in SEQ ID NO: 1 is useful. The inhibitory action on growth of cancer cells also includes a cancer cell-killing action. It is presumed that any actions of the antisense oligonucleotide of the present invention are based on the inhibitory action on the canceration ability and the like of U5 RNA. Here, the inhibitory action of the antisense oligonucleotide of the present invention on growth of cancer cells can be confirmed according to a method described in the Examples described later.

The method of synthesizing the antisense oligonucleotide of the present invention is not particularly limited, and methods using a known oligonucleotide synthesizer, such as a phosphoroamidite method, a phosphorothioate method, a phosphotriester method and the like can be used.

For increasing the stability of the antisense oligonucleotide of the present invention and the affinity thereof for cells, it is possible to use a derivative obtained by substituting a hydroxyl group in the phosphate group or in the ribose moiety with another stable group in such a range as not to significantly decrease its activity. Specific examples of such antisense oligonucleotide derivatives include derivatives wherein the phosphate group is substituted with a thiophosphate group, a methyl phosphonate group and the like, or a hydroxyl group in the ribose moiety is substituted with an alkoxy group such as a methoxy group, an allyloxy group or the like or with an amino group, a fluorine atom and the like.

In molecular design of the antisense oligonucleotide of the present invention, a nucleotide sequence constituting the antisense oligonucleotide is important, and the oligonucleotide includes, in addition to naturally occurring nucleic acid molecules, the non-natural modified oligonucleotides described above, and may be peptide nucleic acid-type modified compounds (PNAs). The antisense oligonucleotide of the present invention is preferably the one having a sugar (preferably pentose) structure in its structure because it is excellent in permeability through a cell membrane, a nuclear membrane and the like.

The antisense oligonucleotide of the present invention may be DNA type or RNA type, but the DNA type is preferable from the viewpoint of higher stability upon administration into the living body.

The antisense oligonucleotide of the present invention can also be used alone. Accordingly, the inhibitor of cancer cell growth and the therapeutic or prophylactic agent for cancer provided according to the present invention (hereinafter, sometimes referred to collectively as pharmaceutical preparation) may consist of said antisense oligonucleotide as it is, but are preferably those prepared by mixing the antisense oligonucleotide with a pharmaceutically acceptable material and forming the mixture into a pharmaceutical preparation by a known method. Here, although the inhibitor of cancer cell growth and the therapeutic or prophylactic agent for cancer are not particularly distinguished from each other in respect of the composition, production process and the like, the two are different in that the inhibitor of cancer cell growth is intended for, in addition to use in relieving or ameliorating the symptom of a cancer or in treating or preventing a cancer, use in suppression of cancer cell growth, for example as a general reagent in a usual experimental process. The pharmaceutical preparation can be produced for example in the following manner.

For example, an injection can be prepared by dissolving the antisense oligonucleotide of the present invention in water, physiological saline, a glucose solution and the like, and may contain a buffering agent, a preservative, a stabilizer or the like if necessary.

An ointment can be prepared by dissolving or dispersing the antisense oligonucleotide of the present invention in a fat-and-oil-based, emulsion-based or water-soluble base material, and may contain a stabilizer, a pH adjusting agent, a plasticizer, an emulsifier, a surfactant, a solubilizer, a wetting agent, a preservative, an antiseptic, a solvent, an absorption accelerator and the like if necessary.

An emulsion, a lotion and the like can be prepared by dissolving or dispersing the antisense oligonucleotide of the present invention in an aqueous phase, then emulsifying it with an oil phase component such as a hydrocarbon or higher alcohol, and may contain a stabilizer, a pH adjusting agent, a plasticizer, an emulsifier, a surfactant, a solubilizer, a wetting agent, a preservative, an antiseptic, a solvent, an absorption accelerator or the like if necessary.

The cell growth inhibitor of the present invention may be prepared as a dry product which can be formed easily into a solution by adding, for example water as a general reagent.

When more efficient incorporation of the antisense oligonucleotide of the present invention into the living body or duration of the effect is desired, the antisense oligonucleotide is preferably combined with a pharmaceutically acceptable known carrier to form a pharmaceutical preparation. The carrier includes, for example, carriers based on lipid such as liposomes, fat emulsion and micelles, peptide carriers such as polylysine and polyornithine, and synthetic polymer carriers such as polyethylene imine and polylactic acid/glycolic acid copolymers. In particular, a pharmaceutical preparation combined with liposomes is preferable. In the pharmaceutical preparation, the antisense oligonucleotide of the present invention is present preferably in a form embedded in liposomes. Formulation using these carriers can be carried out according to a known method.

For example, a method of formulation using liposomes is described by Gregory, G. (ed), Liposome Technology: *Liposome Preparation and Related Techniques*, 2$^{nd}$ Ed., CRC Pr., 1992, and the like. The pharmaceutical preparation combined with liposomes may contain not only lipid such as phospholipid, glycolipid and neutral lipid usually used in formation of liposomes, but also substances giving cationic charge to formed liposomes, for example, dicetyl phosphoric acid, stearyl amine and the like, and substances preventing oxidation of liposomes, for example, α-tocopherol and the like. For the purpose of enhancing incorporation into cells or increasing directivity to a target cell, the above carriers arbitrarily modified can be used.

Here, these pharmaceutical preparations may contain other known components of which anti-carcinogenicity is recognized.

In the above pharmaceutical preparation, the antisense oligonucleotide of the present invention can be used after ligation to a vector, i.e., integration into an arbitrary vector. In this case, the antisense oligonucleotide is preferably ligated operatively to a suitable promoter. The term "operatively" means that the antisense oligonucleotide (RNA) can be expressed in cells of a living body by the action of the promoter. The vector includes, but is not limited to, for example, an adenovirus vector, a vaccinia virus vector, a retrovirus vector and the like. Such vector is useful as a vector for gene therapy. For a method of constructing such vector, a specific usage thereof, and the like, literatures such as Sambrook, J., et al., Molecular Cloning: *A Laboratory Manual;* 2$^{nd}$ Ed., Cold Spring Harbor Laboratory, Cold Spring Harbor, N.Y., 1989, and the like may be referred to.

The content of the antisense oligonucleotide in the pharmaceutical preparation of the present invention is not particularly limited, and may be suitably regulated so as to achieve a desired effect depending on use for each pharmaceutical preparation. Usually a content of around 1 to 10% by weight is suitable.

The inhibitor for cancer cell growth and the therapeutic or prophylactic agent for cancer of the present invention are obtained in the manner described above. Accordingly, a method of using the antisense oligonucleotide of the present invention in production of the inhibitor for cancer cell growth or the therapeutic or prophylactic agent for cancer according to the present invention is provided as another embodiment of the present invention.

The method of administering the therapeutic or prophylactic agent for cancer of the present invention into the living body includes, but is not particularly limited to, for example, oral administration, intravenous administration, transdermal administration, topical administration, intraperitoneal administration and the like depending on the form of the therapeutic or prophylactic agent. As the method of administering the therapeutic or prophylactic agent for cancer according to the present invention, a more effective method may be selected depending on the conditions and the like of each individual and each disease, and usually, intravenous administration is preferable. The dose of the therapeutic or prophylactic agent for cancer may be determined suitably depending on symptom and the like, and is not particularly limited. In the case of intravenous administration, the dose of the therapeutic or prophylactic agent for cancer is, in terms of the amount of the antisense oligonucleotide of the present invention, preferably from 0.1 to 1 mg/(body weight) kg, more preferably from 0.1 to 0.5 mg/(body weight) kg per day in a human. Administration may be carried out once per day or plural times with divided portions per day. The administration period is also not particularly limited.

Here, the living body into which the therapeutic or prophylactic agent for cancer of the present invention is administered is not limited to the humans mentioned above, and includes, for example, mammalians and the like other than humans. The inhibitor of cancer cell growth according to the present invention can also be used in the same manner as for the therapeutic or prophylactic agent for cancer of the present invention.

The location of the cancer cells as the target of the anti-carcinogenicity of the inhibitor for cancer cell growth and the therapeutic or prophylactic agent for cancer of the present invention is not particularly limited, and particularly the cancer cells are preferably derived from a body surface such as skin; digestive tracts such as esophagus, stomach and large intestine; a liver into which the inhibitor or the agent can be intra-arterially administered; and the like.

Here, no particular toxicity is recognized in the antisense oligonucleotide of the present invention as shown for example in Reference Example 1 described later.

EXAMPLES

Hereinafter, the present invention is described by reference to the Examples, but the present invention is not limited to these examples.

Example 1

Since the transforming RNA participates in canceration of cells and suppression of synthesis of secretory protein, it is presumed that suppression of synthesis of secretory protein is involved in canceration of cells. On the other hand, the antisense ODN (SEQ ID NO: 6) acts for reducing suppression of synthesis of secretory protein, and thus the antisense ODN is expected to work against canceration.

Accordingly, antisense oligonucleotide (phosphorothioate oligos) to a nucleotide sequence consisting of several residues, the center of which had a nucleotide sequence (SEQ ID NO: 8) of positions 48 to 51 of 7SL RNA of SRP derived from rabbit cells, were synthesized and examined for their influence on human cancer cells by incorporation from out of the cells. It is known that the nucleotide sequence of 7SL RNA derived from human cells has the same nucleotide sequence as that derived from rabbit cells.

Antisense oligonucleotides (DNAs) having the nucleotide sequences shown in Table 1 below were prepared by making a request to TAKARA BIO INC. In the table, oligos 1 to 5 are the names of antisense oligonucleotides, and numbers in the parentheses indicate the corresponding position of the nucleotide sequence of 7SL RNA. The oligo 5 is a mixture of antisense oligonucleotides prepared at random independently of the nucleotide sequence of 7SL RNA, and N stands for A, C, G or T.

TABLE 1

| Oligo 1 | CCTC (48-51) |
| Oligo 2 | GCCTC (48-52) |
| Oligo 3 | CCTCA (47-51) |
| Oligo 4 | GCCTCA (47-52) |
| Oligo 5 | NNNNN |

The influence of each oligo on cell growth was examined. Specifically, HeLa cells, which are human cancer cells in a DMEM medium containing 10% heat-inactivated fetal calf serum (FCS), were seeded at a density of 1500 cells/well in a 96-well plate. After culture for 24 hours, the culture solution was exchanged with a culture solution containing each oligo at a concentration of 10 μM and 1% FCS. The cells were cultured at 37° C. in the presence of $CO_2$. Thereafter, the ratio of living cells [survival ratio of cells (%)] was examined over 4 days at 24-hour intervals (absorbance: 450 to 650 nm) by a modified MTT method (WST-1+1-methoxy PMS) using a cell counting kit (manufactured by DOJINDO). Here, a culture solution exchanged with a culture solution not containing any oligo was used as a control (this applies hereinafter).

Figure 2:
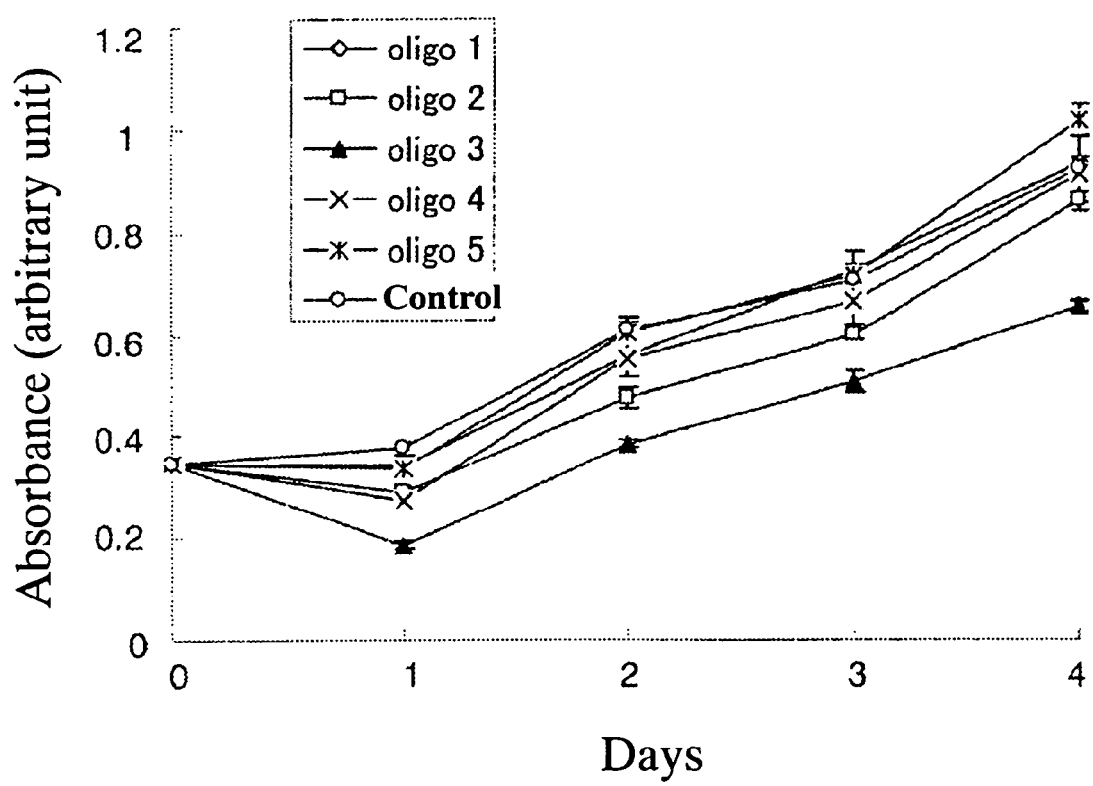
FIG. 2 is a graph showing the influence of oligos 1 to 5, which are antisense oligonucleotides prepared in the Examples, on growth of human cancer cells.

FIG. 2 is a graph showing the influence of each oligo on growth of human cancer cells. The experiment was conducted in triplicate. In the graph, each datum is shown in mean±SD (this applies hereinafter). In the oligo 3, the survival ratio of the cells is lowest, indicating the highest inhibitory effect on growth of the human cancer cells. The survival ratios of the cells on Days 1, 2, 3 and 4 were 49.6%, 62.7%, 71.6% and 71.1% to the control, respectively.

Then, an experiment was conducted in a similar manner, setting the concentration of the oligo 3 in the culture solutions at 2.5, 5, 10 and 20 μM respectively, to examine the relationship between the inhibition of growth of human cancer cells and the concentration.

Figure 3:
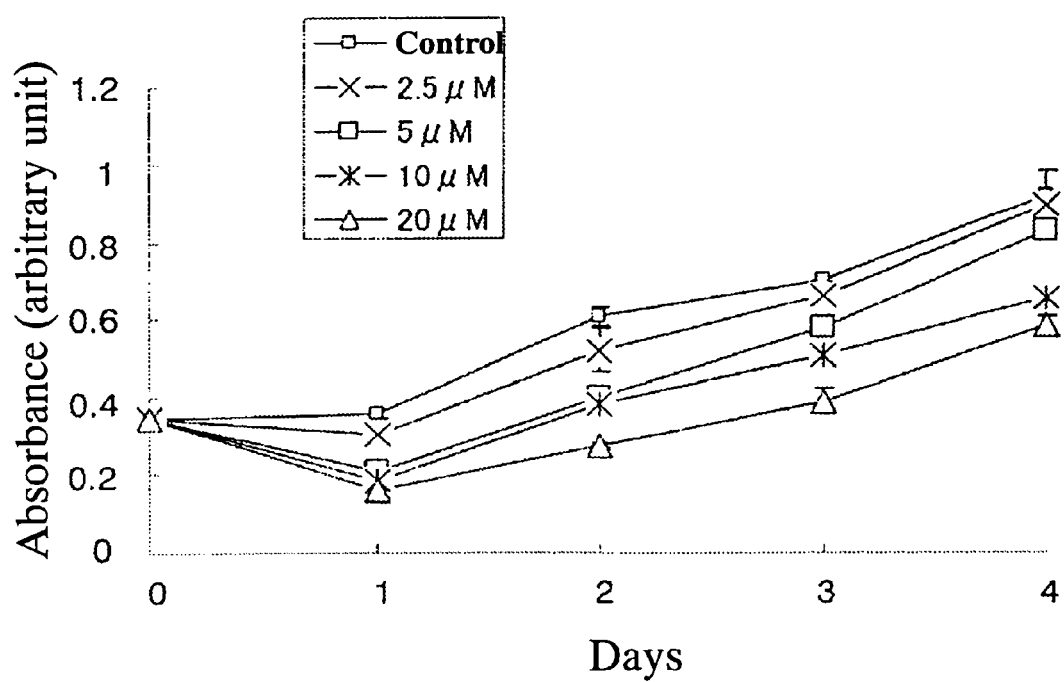
FIG. 3 is a graph showing the concentration-dependent influence of oligo 3 on growth of human cancer cells.

FIG. 3 is a graph showing the concentration-dependent influence of oligo 3 on growth of human cancer cells. It can be seen that the inhibition of growth of human cancer cells by the oligo 3 is increased in proportion to the concentration. The survival ratios of the cells on Days 1, 2, 3 and 4 were 44.4%, 45.1%, 55.5% and 63.8% to the control, respectively.

The influence of each oligo on DNA synthesis of cells was examined by observing the incorporation of [$^3$H]-methylthymidine into cells. Specifically, the cells were cultured for 24 hours in the same manner as described above, and then the culture solution was exchanged with a culture solution containing each oligo at a concentration of 5, 10 or 20 μM and 0.1% FCS. After 18 hours, 1 μCi/mL [$^3$H]-methylthymidine was added to the culture solution, and the cells were cultured for another 6 hours. After culture, the specific radioactivity of the cells after predetermined treatment was determined with a liquid scintillation counter.

Figure 4:
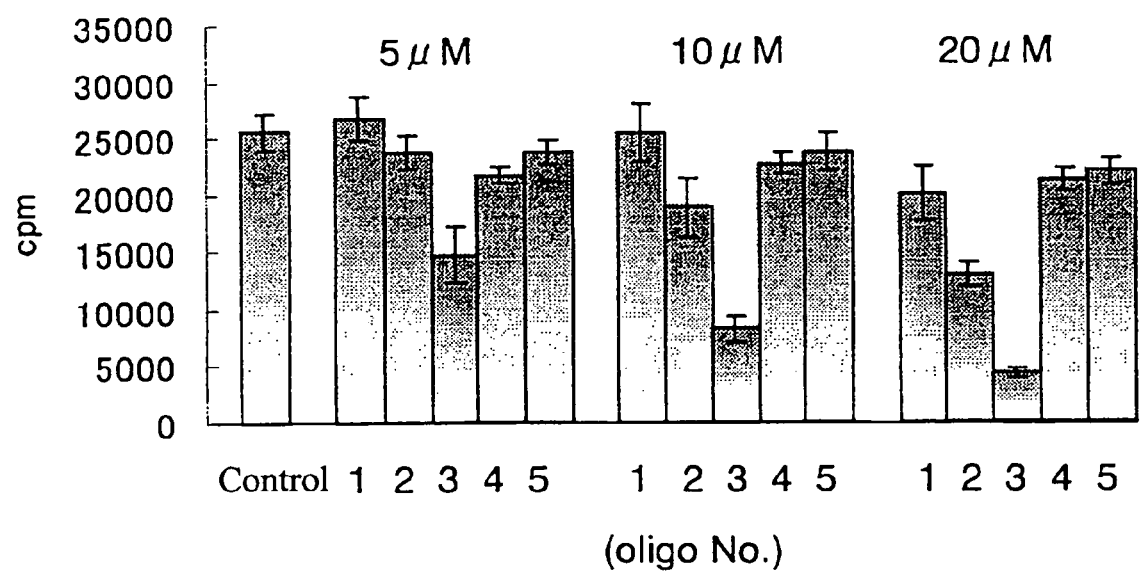
FIG. 4 is a graph showing the influence of oligos 1 to 5 on DNA synthesis of cells in human cancer cells.

FIG. 4 is a graph showing the influence of each oligo on DNA synthesis of cells in the human cancer cells. It can be seen that the incorporation of [$^3$H]-methylthymidine into the cells was suppressed to the lowest level by the oligo 3, and the inhibitory effect of the oligo 3 on growth of the human cancer cells was strong. The incorporation ratios of [$^3$H]-methylthymidine into the human cancer cells in the presence of the oligo 3 at concentrations of 5, 10 and 20 μM were 57.5%, 32.0% and 16.6% to the control, respectively.

Further, the induction of cell death of the human cancer cells by the oligo 3 was examined. Specifically, 3,000 HeLa cells were seeded in a slide chamber. After culture for 24 hours, the culture solution was exchanged with a culture solution containing the oligo 3 at a concentration of 20 μM. About 18 hours after addition of the oligo 3, the cultured cells were observed with a stereoscopic microscope (100 magnifications; manufactured by Olympus Corporation), and as a result, a process of from shrinkage of cells to cell death was observed. Furthermore, 24 hours after addition of the oligo 3, the cells were washed with phosphate buffered saline (PBS) and then subjected to Giemsa staining to determine the numbers of living cells and dead cells, and the survival ratio of the cells (%) was determined from the obtained numbers of the cells. Here, the oligo 5 was used additionally as a control.

Figure 5:
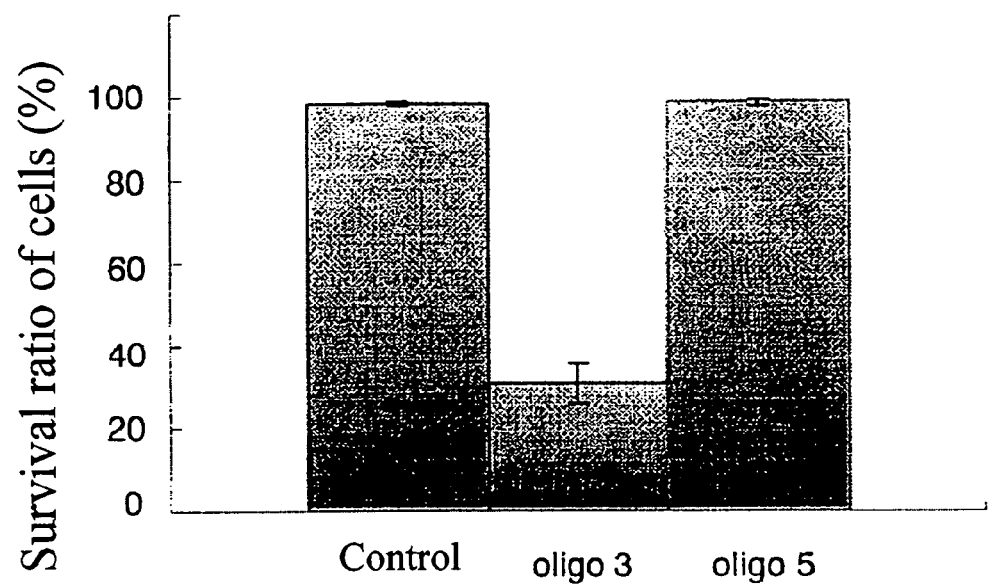
FIG. 5 is a graph showing the influence of oligo 3 on death of human cancer cells.

FIG. 5 is a graph showing the influence of the oligo 3 on death of human cancer cells. The survival ratio of the cells with the oligo 3 is 30.8%, while the survival ratios of the cells in the control and with the oligo 5 are 98.5% and 98.7% respectively, indicating that the survival ratio of the cells with the oligo 3 is significantly lower than the other controls, and thus it can be seen that the oligo 3 has a strong inducing action for cell death on human cancer cells.

As can be seen, the oligo 3 (SEQ ID NO: 1), which is an antisense oligonucleotide to the nucleotide sequence in positions 47 to 51 of 7SL RNA of SRP, suppresses growth of cancer cells and has an action of inducing cell death thereof. Accordingly, the utility of the oligo 3 as a carcinostatic is expected.

Reference Example 1

The toxicity of the oligo 3 was examined. Specifically, the oligo 3 was dissolved in a physiological saline so as to have a concentration of 1 mg/mL and administered intravenously into female mice (5-week-old) in a dose of 20 μg per g of the body weight. On the day of administration (Day 0) and 2, 5, 10, 12 and 14 days after the administration, the weight of each mouse was determined.

Figure 6:
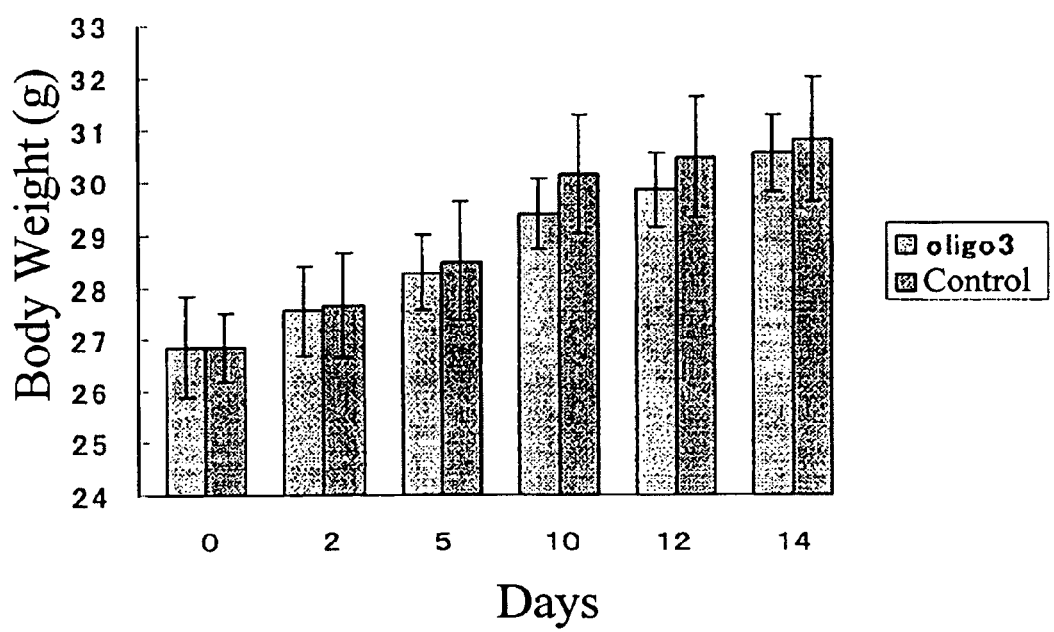
FIG. 6 is a graph showing the influence of oligo 3 on increase in weight of mice in the case of intravenous administration in a dose of 20 μg/(body weight) g.

FIG. 6 is a graph showing the influence of the oligo 3 on increase of the body weight of the mouse in the case of intravenous administration in a dose of 20 μg/(body weight) g. In the graph, each datum is shown in mean±SE. Here, the data were obtained by using 7 mice for the oligo 3 and 6 mice for the control, respectively.

As shown in FIG. 6, there was no difference between the oligo 3 and the control in respect of the influence on increase of the body weight. Generation of symptoms particularly different between the two was not recognized. From these results, it is considered that the oligo 3 does not exhibit toxicity particularly.

According to the present invention, there is provided an antisense oligonucleotide having anti-carcinogenicity such as, for example, an inhibitory action on growth of cancer cells and a therapeutic or prophylactic action on cancer, as well as an inhibitor of cancer cell growth and a therapeutic or pro-phylactic agent for cancer, which comprise the antisense oligonucleotide. These can contribute significantly to the field of cancer therapy.

Sequence Listing Free Text

SEQ ID NO: 1 is a nucleotide sequence of an antisense oligonucleotide to a nucleotide sequence of positions 47 to 51 of 7SL RNA.

SEQ ID NO: 3 is a partial nucleotide sequence of a transforming RNA.

SEQ ID NO: 4 is a nucleotide sequence of an oligodeoxynucleotide prepared on the basis of the partial nucleotide sequence of the transforming RNA.

SEQ ID NO: 5 is a partial nucleotide sequence of an oligodeoxynucleotide.

SEQ ID NO: 6 is a nucleotide sequence of an antisense oligodeoxynucleotide to the nucleotide sequence of the oligodeoxynucleotide.

SEQ ID NO: 7 is a partial nucleotide sequence of the antisense oligodeoxynucleotide.

---

The invention claimed is:

1. An antisense oligonucleotide to a nucleotide sequence of positions 47 to 51 of 7SL RNA of a signal recognition particle (SRP), wherein said antisense oligonucleotide consists of the nucleotide sequence of SEQ ID NO: 1.

2. An inhibitor of cancer cell growth comprising the antisense oligonucleotide as defined in claim 1.

3. A therapeutic or prophylactic agent for cancer comprising the antisense oligonucleotide as defined in claim 1.

4. The therapeutic or prophylactic agent according to claim 3, wherein the antisense oligonucleotide is present in a liposome.

5. A method for preparing a pharmaceutical composition comprising mixing the antisense oligonucleotide according to claim 1 with a pharmaceutically acceptable carrier.

* * * * *